United States Patent
Sell

(10) Patent No.: US 6,562,019 B1
(45) Date of Patent: May 13, 2003

(54) METHOD OF UTILIZING A MAGNETICALLY GUIDED MYOCARDIAL TREATMENT SYSTEM

(75) Inventor: Jonathan C. Sell, Eagan, MN (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/398,686

(22) Filed: Sep. 20, 1999

(51) Int. Cl.$^7$ .............................................. A61M 31/00
(52) U.S. Cl. ........................... 604/510; 128/898; 606/15
(58) Field of Search .............................. 604/21, 22, 48, 604/500, 164.01, 264, 95.01; 606/108, 2, 7, 13–16; 128/898; 600/310, 342, 473, 476, 2, 101, 108; 607/1, 88, 89, 92, 94

(56) References Cited

U.S. PATENT DOCUMENTS

| | | | |
|---|---|---|---|
| 5,263,493 A | | 11/1993 | Avitall |
| 5,324,284 A | | 6/1994 | Imran |
| 5,327,889 A | | 7/1994 | Imran |
| 5,391,199 A | | 2/1995 | Ben-Haim |
| 5,429,131 A | * | 7/1995 | Scheinman et al. .......... 128/642 |
| 5,443,489 A | | 8/1995 | Ben-Haim |
| 5,454,370 A | | 10/1995 | Avitall |
| 5,476,495 A | | 12/1995 | Kordis et al. |
| 5,480,422 A | | 1/1996 | Ben-Haim |
| 5,487,385 A | | 1/1996 | Avitall |
| 5,507,744 A | * | 4/1996 | Tay et al. ...................... 606/50 |
| 5,546,951 A | | 8/1996 | Ben-Haim |
| 5,568,809 A | | 10/1996 | Ben-Haim |
| 5,694,945 A | | 12/1997 | Ben-Haim |
| 5,713,946 A | | 2/1998 | Ben-Haim |
| 5,718,241 A | | 2/1998 | Ben-Haim et al. |
| 5,738,096 A | | 4/1998 | Ben-Haim |
| 5,752,513 A | | 5/1998 | Acker et al. |
| 5,766,164 A | * | 6/1998 | Mueller et al. ................ 606/15 |
| 5,769,843 A | * | 6/1998 | Abela et al. ................... 606/10 |
| 5,810,836 A | * | 9/1998 | Hussein et al. .............. 606/108 |
| 5,840,025 A | | 11/1998 | Ben-Haim |
| 5,846,198 A | | 12/1998 | Killmann |
| 5,921,244 A | * | 7/1999 | Chen et al. ................... 128/897 |
| 5,980,548 A | * | 11/1999 | Evans et al. ................. 606/185 |
| 6,015,414 A | * | 1/2000 | Werp et al. .................. 606/108 |
| 6,056,743 A | * | 5/2000 | Ellis et al. ..................... 606/15 |
| 6,464,693 B1 | * | 10/2000 | Andrews et al. ............... 606/15 |
| 6,196,230 B1 | * | 3/2001 | Hall et al. .................... 128/898 |
| 6,203,556 B1 | * | 3/2001 | Evans et al. ................. 606/185 |
| 6,224,566 B1 | * | 5/2001 | Loeb ............................ 604/22 |
| 6,248,112 B1 | * | 6/2001 | Gambale et al. ............. 606/108 |
| 6,298,257 B1 | * | 10/2001 | Hall et al. .................... 600/407 |

* cited by examiner

Primary Examiner—Brian L. Casler
Assistant Examiner—Jennifer Maynard
(74) Attorney, Agent, or Firm—Harness Dickey & Pierce, P.L.C.

(57) ABSTRACT

A magnetically tipped catheter is used t tunnel into the myocardium for cardiac treatment.

3 Claims, 4 Drawing Sheets

METHOD OF UTILIZING A MAGNETICALLY GUIDED MYOCARDIAL TREATMENT SYSTEM

FIELD OF THE INVENTION

The present invention is related to the medical treatment of the myocardium and more specifically to devices for accessing the myocardium and to techniques for magnetically guided myocardial interventions.

BACKGROUND OF THE INVENTION

Various diseases exist that require precise access to the heart muscle. Current treatment modalities have been limited by the ability to direct and hold treatment devices in the proper location in a beating heart. Consequently, major open surgical interventions are common where a minimally invasive approach would be preferable. One such procedure is myocardial revascualrization and the inventions are described in that context.

For example patients who exhibit ischemic heart disease and who experience angina can be treated by perforating the wall of the ventricle. It is not entirely understood why this form of injury improves the cardiac performance of the patient. Some evidence suggests that the healing response to the injury causes new blood vessels to form and increases the size of existing blood vessels. The additional blood flow relives the symptom angina.

The first myocardial revascularization experiments were performed with a laser, which was used to perforate the heart from the "outside" of the heart. In general the laser energy was applied to the exterior wall of the ventricle and activated. In use the laser energy burns and chars a hole in the heart wall. The blood pool inside the heart prevents further injury to structures within the heart.

More recently it has been proposed to revascularize the heart wall though a percutaneous transluminal approach. See for example Nita U.S. Pat. No. 5,827,203. This technique can be used to place a catheter against the endocardial surface of the heart. However the heart wall is in constant motion and this relative motion renders creation of the lesion problematic.

In general, both improved devices and techniques are needed to advance this therapy.

SUMMARY

The methods and devices of the invention are useful in a variety of settings. For purposes of illustration the invention is described in the context of myocardial revascularization which is one instance where the catheter is magnetically navigated to a site near a wall of the heart. Other examples of treatments include the repair of septal defects and heart biopsy. It is anticipated that some forms of cardiomyopathy may respond to therapies delivered with these tools as well. For this reason it must be understood that the devices and methods can be used in a variety of contexts within the body.

A magnetically navigable and controllable catheter device is deployed at the heart wall and this device tunnels into the myocardium. Any of a variety of canalization technologies can be used to tunnel into the heart wall causing mechanical disruption of the tissues, including mechanical needles and RF energy sources as well as direct laser and heated tips. The catheter device is guided by externally applied magnetic fields that are created by a magnetic surgery system (MSS). The MSS applies magnetic fields and gradients from outside the body to manipulate and direct medical devices within the body. The catheter devices of the present invention include magnetic elements that respond to the MSS field or gradient.

In general the physician interacts with a workstation that is associated with the MSS. The physician may define paths and monitor the progress of a procedure. Fully automatic and fully manual methods are operable with the invention.

Although several energy sources are disclosed that can be delivered by the catheter trough its distal tip, an RF heated tip is preferred since it can be used both to cut and to coagulate tissues depending on the delivered energy level. This feature is shared with laser-heated tips and other thermal catheter technologies but RF devices have a greater history of use for coagulation.

The proposed methods of the invention can be used to move the catheter device both along and across muscle planes within the heart tissue so that a complex wound pathway or "tunnel" can be created. This structured shape can be used to retain "implant" materials such as growth factor. Growth factor or other drugs may be embedded in or on absorbable material. In some instances it may be desirable to combine the drug with a magnetic particle so that the gradient and fields can be used to position and retain the drug in the tissue. For example the lesion can be in the form of a "blind" hole and the drug can be left behind in the wound and retained magnetically inside the tissues.

For purposes of this discussion the term "ablation" or "lesion" should be considered to include thermally damaged tissues eroded and charred tissue and other processes that destroy or remove tissue. Typical devices to carry out this "injury" include mechanical RF electrical Thermal optical and ultrasonic means. Throughout the description the wound is referred to as a tunnel in recognition of its shape.

BRIEF DESCRIPTION OF THE DRAWINGS

Throughout the various figures of the drawing identical reference numerals are used to indicate identical or equivalent structure, wherein.

DETAILED DESCRIPTION OF ILLUSTRATIVE EMBODIMENTS

Figure 1:
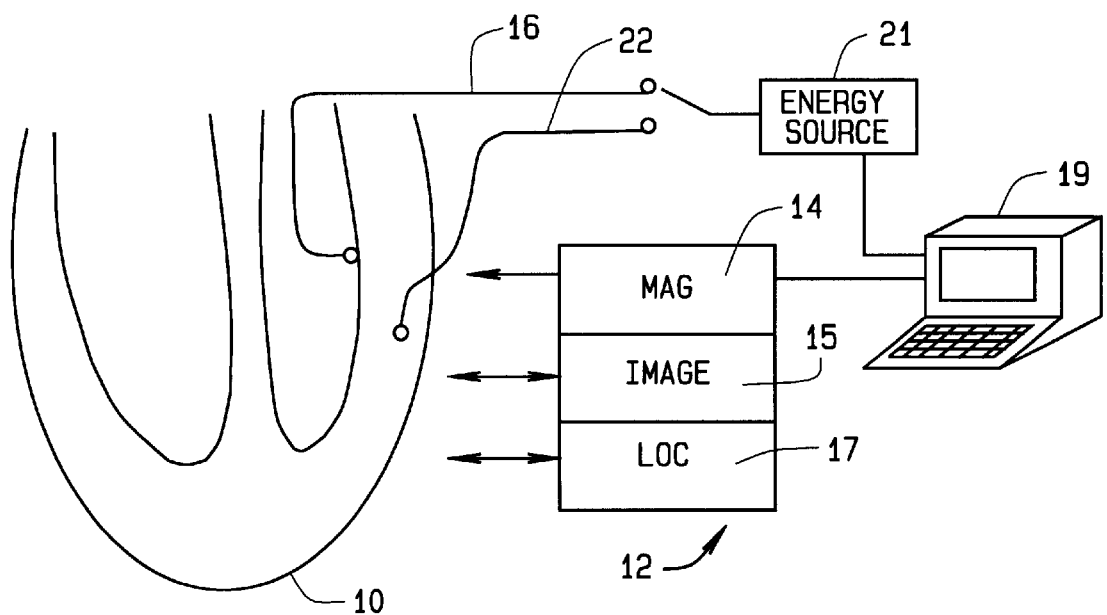
FIG. 1 is a schematic of a heart showing two surgical approaches.

FIG. 1 shows a schematic heart 10 located within the patient interacting with a magnetic surgery system or MSS 12. Two different surgical approaches are shown in the figure represented by catheter 16 and catheter 22.

The MSS system 12 includes a magnet system 14, which can generate controlled fields and gradients within the patient. The MSS 12 may also optionally include a localization system 17, which can be used to find the location and direction of the catheter tip within the body. The MSS 12 may also optionally include an imaging system 15, which can be used display, the real time location of the catheter with respect to the tissues. The imaging system 15 can also be used to collect preoperative images to guide the procedure. A companion workstation 19 is interfaced with these systems and controls them through software. In use the physician interacts with the MSS 12 through the workstation 19. It should be noted that the energy source for the revascualrization catheter is under the control of the MSS as well so that the therapy is integrated through the workstation. In general the advancement of the catheter can be performed directly by the physician or the process may be automated through the workstation. For these reasons the invention contemplates both fully manual and fully automatic procedures mediated by the MSS.

Catheter 16 is depicted in a ventricle for a therapeutic intervention. This catheter shows a percutaneous transluminal access of the ventricle. Catheter 22 is shown in contact with the ventricle through an incision in the chest. This catheter shows a pericardial access to the epicardial surface of the heart 10. Catheters may also approach the heart through a site in the coronary tree. Although three different approaches are shown or described, the remainder of the description is disclosed in the context of the preferred transluminal approach for simplicity and clarity of disclosure. It should be recognized that the devices and procedures might be used in the other approaches as well.

Figure 2:
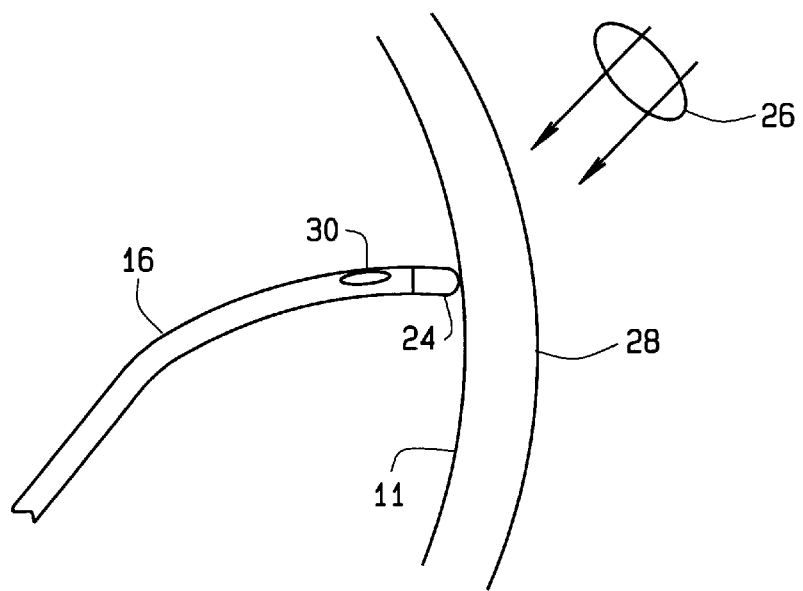
FIG. 2 is a representation of a step in the method.

FIG. 2 shows a catheter 16 in contact with the endocardial surface 11 of the heart. The distal tip 24 may include a magnetic or magnitizable material that interacts with the MSS fields 26. One distinct advantage of this approach is that the applied field creates a force that holds the tip 24 in contact with the moving myocardial wall 28. Once an appropriate starting position has been established the tip 24 is activated through the workstation 19 and the catheter enters the myocardial wall 11 seen best in FIG. 3.

Figure 3:
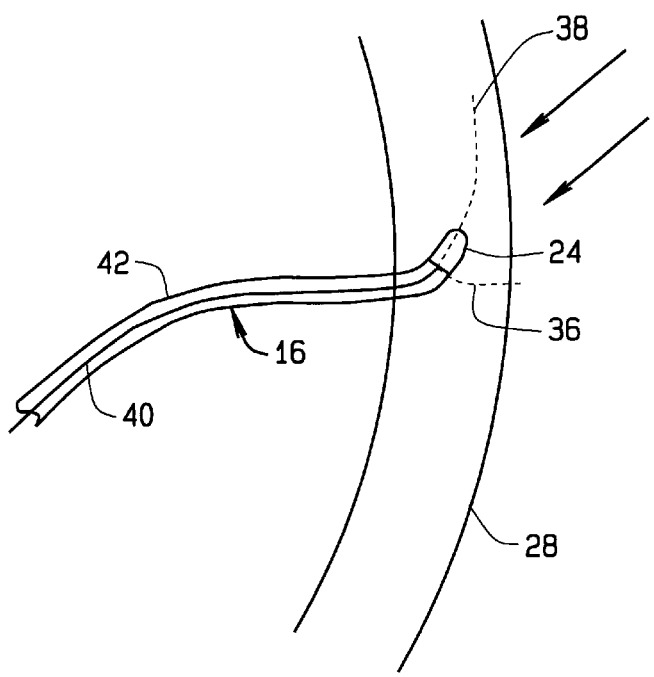
FIG. 3 is a representation of a step in the method.

FIG. 3 shows the tip 24 turning under the influence of the MSS. A primary entrance axis is defined and shown in the figure as axis 36 while the instantaneous direction of travel is shown as path 38. It is a property of the device 16 that it can track in the tissue and turn from an entry path through approximately 90 degrees within the distance of the heart wall.

Figure 4:
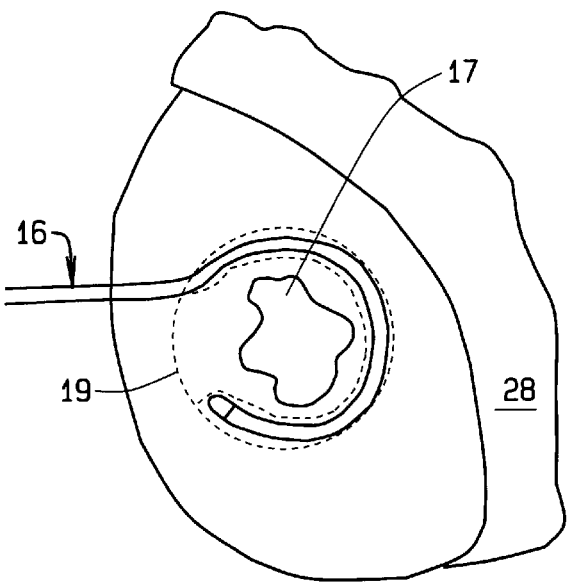
FIG. 4 is a representation of a step in the method.

FIG. 4 is an example of the use of the system to treat an infarcted region 17 of the heart by encircling it with an ablation path within the wall 28 of the heart In use the MSS system is used to define the circular path indicated in the figure as path 19.

Figure 5:
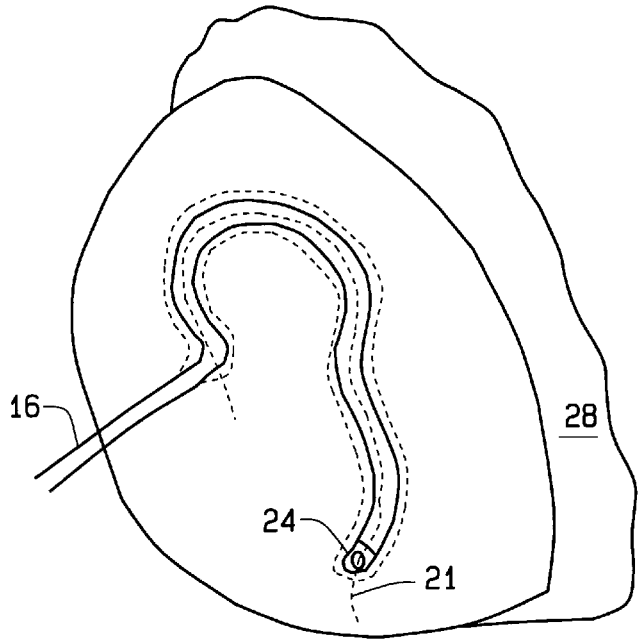
FIG. 5 is a representation of a step in the method.

FIG. 5 shows the catheter 16 being used to define a very complex path within the heart wall 28. The MSS defines the arcuate path 21 and the magnetic tip 24 of the catheter 16 follows the path. In use the ablation energy source is sufficient to tunnel in the tissue. Ablation wounds for this nature may be used to treat "hibernating tissue" with drugs and the like.

Figure 6:
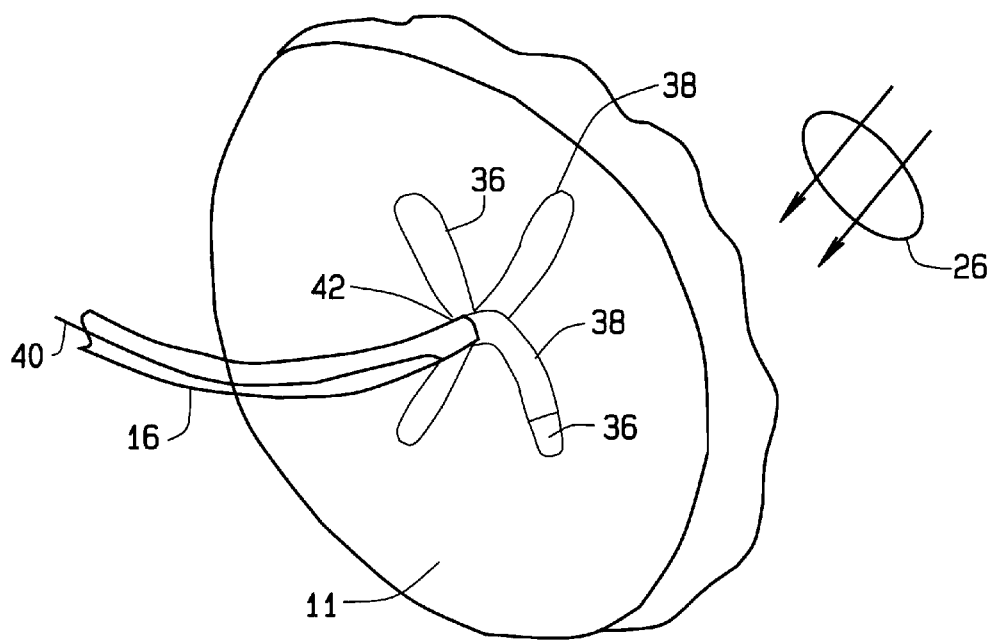
FIG. 6 is a representation of a step in the method.

FIG. 6 shows a guided intervention with the myocardial tissues. The MSS 12 can be used to define a path for the tip 24 of the catheter 16. A simple straight through path is depicted as path 38. This path takes the catheter 16 tip 24 completely through the block of tissue 11. The curved path is shown as path 36 which turns within the tissue so that the tip 24 is retained in the myocardium. In the illustration the tip 24 is following the curved path 36. In this example the tip enters the tissue at an approximately orthogonal angle and remains within the myocardial tissues and creates a blind "wormhole" lesion or path. A lumen 40 in the catheter body 42 can be used to deliver a drug such as growth factor to the site of the injury. Other candidate drugs contemplated within the scope of the disclosure include VEGF vascular endothelial growth factor aFGF acidic fibroblast growth factor and bFGF basic fibroblast growth factor. It is believed that the uptake of the drug will be effective and result in the rapid development of new vessels. FIG. 6 shows a set of wormhole tracks, which share a common entry point 42. In operation the catheter body may be retracted along the track and repositioned with the MSS to create a complex series of lesions that share the common entry point forming a "star" shaped system of tunnels. Upon retraction out of the tissue the power level at the tip 24 can be reduced and the tip can "cauterize" or seal the opening entry point 42.

Figure 7:
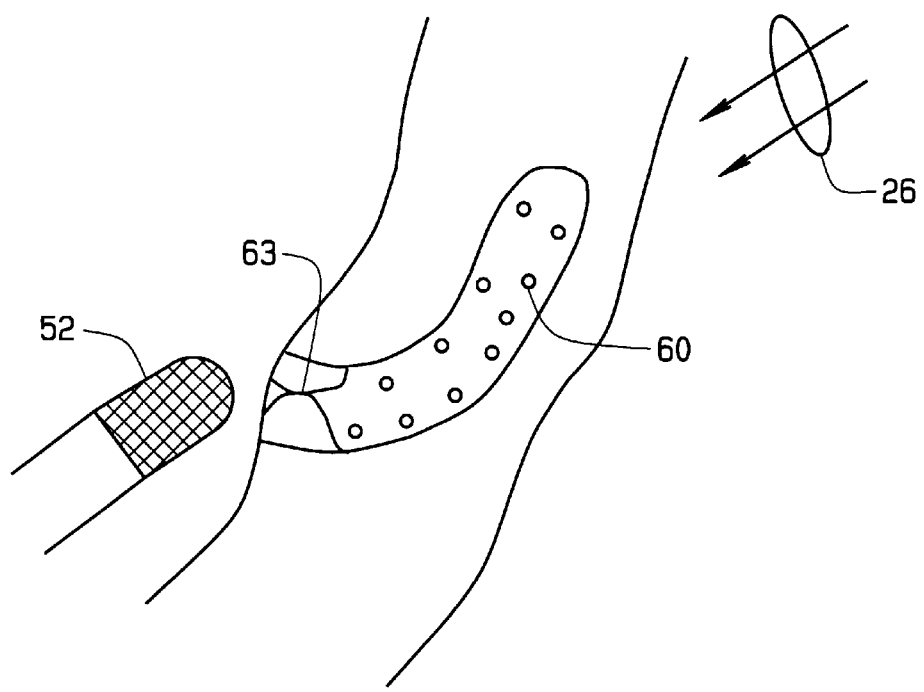

FIG. 7 shows a preferred therapy where a RF heated catheter is used to create a "wormhole" lesion under the control of the field 26. During withdrawal of the catheter deposit drug coated magnetic particle typified by particle 60. The distal tip 52 cauterizes the tissue on the exit path coagulating tissue shown as plug 63.

Figure 8:
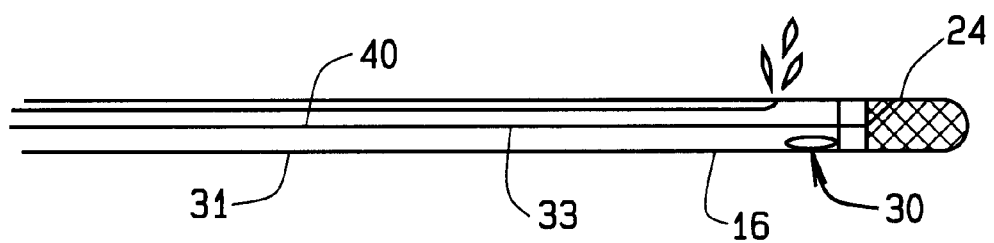
FIG. 8 is a schematic of an exemplary thermal catheter.

FIG. 8 shows an illustrative but preferred catheter 16. The preferred tunneling energy is a heated tip 24 which may accomplished with either radio frequency (RF) or laser energy through an optical fiber 33 from the energy source 21.

Localization coils 30 or the like in the catheter body 31 maybe used with the MSS to reveal the real time location of the catheter. Real time biplane fluoroscopy can also be used to show the physician the location of the device against the wall. The coils or other structures may be included to increase the radiopacity of the catheter tip.

Figure 9:
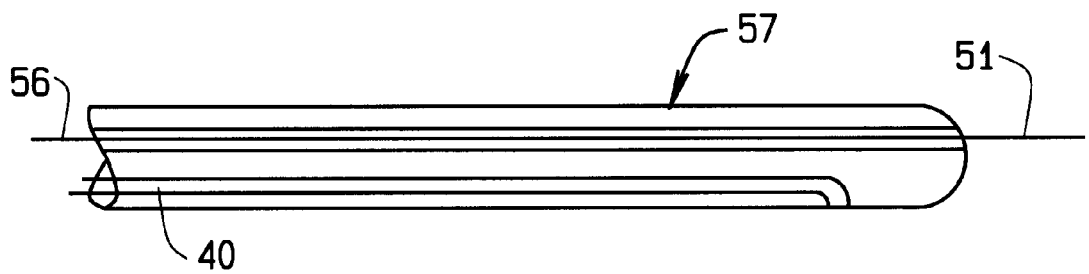
FIG. 9 is a schematic of a mechanical revascularization catheter.

FIG. 9 shows a mechanical catheter with a retractable needle 51, which may be manipulated through the proximal wire 56. In use the needle can be used to pierce the heart wall. The catheter body 57 includes an optional lumen 40, which may be used to deliver a drug during the therapy.

Figure 10:
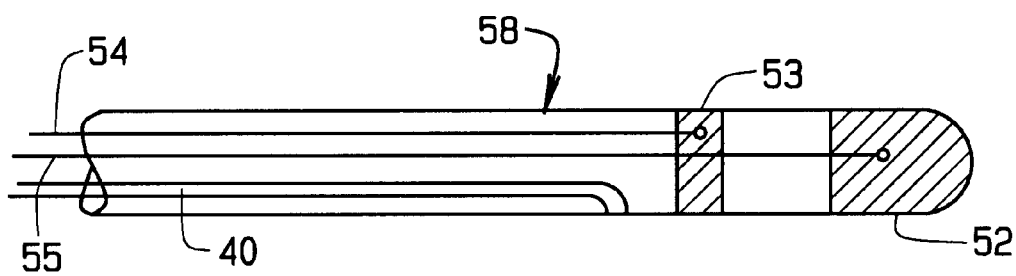
FIG. 10 is a schematic of a RF revascularization catheter.

FIG. 10 is an RF heated bipolar catheter using a distal electrode tip 52 with a proximal indifferent electrode 53 to supply heat to the tissues. An optional lumen 40 is shown for the delivery of a drug. One advantage of the RF catheter is the ability to lower the energy delivered to coagulate tissues.

What is claimed is:

1. A method of treating the heart comprising the steps of:
   navigating a catheter to the myocardium;
   causing the catheter to enter the myocardium assisted by the application of externally generated magnetic fields and gradients, to create a tunnel in the myocardium;
   delivering a magnetically bound drug to the tunnel in the myocardium;
   withdrawing the catheter while retaining the drug in the tunnel with an externally generated magnetic gradient.

2. A method for myocardial treatment comprising the steps of:
   navigating a catheter, having a tip, to a treatment site on the myocardium;
   magnetically holding the tip against the moving surface of the myocardium using an external source magnet;
   applying energy to the tip to form a tunnel into the myocardium;
   injecting a therapeutic agent into the tunnel formed in the myocardium; and withdrawing the catheter and cauterizing the tunnel at a tunnel opening upon exit of the catheter from the tunnel whereby drug left in the tunnel is sealed in the tunnel.

3. A method of treating the heart comprising the steps of:
   navigating a catheter to the myocardium;
   entering the myocardium assisted by the application of externally generated magnetic fields and gradients;
   creating an arcuate tunnel in the myocardium encircling a region of heart tissue; and
   delivering a therapeutic agent to the tunnel in the myocardium.

* * * * *